(12) United States Patent
Liang et al.

(10) Patent No.: US 10,640,469 B2
(45) Date of Patent: May 5, 2020

(54) POLYHYDROXYPHTHALAZINONE COMPOUND, PREPARATION METHOD THEREOF AND USE THEREOF

(71) Applicant: RejuvGen Pharmaceuticals, Inc., Shanghai (CN)

(72) Inventors: Faxiang Liang, Hefei (CN); Yanling Ding, Suzhou (CN)

(73) Assignee: RejuvGen Pharmaceuticals, Inc., Shanghai (CN)

( * ) Notice: Subject to any disclaimer, the term of this patent is extended or adjusted under 35 U.S.C. 154(b) by 0 days.

(21) Appl. No.: 16/562,436

(22) Filed: Sep. 6, 2019

(65) Prior Publication Data

US 2019/0389809 A1    Dec. 26, 2019

Related U.S. Application Data

(63) Continuation of application No. PCT/CN2018/086244, filed on May 10, 2018.

(30) Foreign Application Priority Data

May 23, 2017  (CN) .......................... 2017 1 0369422

(51) Int. Cl.
  *C07D 237/32*   (2006.01)
  *A61K 31/502*   (2006.01)
(52) U.S. Cl.
  CPC .......... *C07D 237/32* (2013.01); *A61K 31/502* (2013.01)
(58) Field of Classification Search
  CPC ...................... C07D 237/32; A61K 31/502
  USPC .......................................... 544/237; 514/248
  See application file for complete search history.

(56) References Cited

PUBLICATIONS

Liu et al., Access to phthalazinones via palladium-catalyzed three-component cycloamino-carbonylation of 2-formylaryl tosylates, hydrazines and CO, Tetrahedron, vol. 72, No. 50, pp. 8282-8286 (2016).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Merck Manual Professional Online Edition, Acute Leukemia, 6 pages, 2013.*

* cited by examiner

*Primary Examiner* — Deepak R Rao

(57) ABSTRACT

The present disclosure provides a polyhydroxyphthalazinone compound, preparation method thereof and use thereof, wherein the general formula of chemical structure of the polyhydroxyphthalazinone compound is shown by the formula (I). The polyhydroxyphthalazinone compound disclosed by the present disclosure has a good effect on activating ERβ receptor, and it is expected to develop a novel ER-β receptor agonist.

8 Claims, No Drawings

POLYHYDROXYPHTHALAZINONE COMPOUND, PREPARATION METHOD THEREOF AND USE THEREOF

CROSS REFERENCE TO RELATED APPLICATIONS

The present application is a continuation of international application No. PCT/CN2018/086244, filed on May 10, 2018, which claims the priority to Chinese patent application no. 201710369422.X, filed on May 23, 2017, both of which are hereby incorporated by reference in its entirety.

TECHNICAL FIELD

The present disclosure belongs to the technical field of biological medicine, and more particularly relates to a polyhydroxyphthalazinone compound, preparation method thereof and use thereof.

BACKGROUND

The estrogen receptor belongs to a steroid nuclear receptor, which is a receptor for nuclear transcription factors induced by ligands. The estrogen receptor is an important cytoregulatory protein that plays a vital role in numerous physiological processes through the endogenous estrogen, including the development and maintenance of secondary sexual characteristics in women, the quality of muscle and bone, etc. The endogenous steroidal estrogen is commonly referred to as a female sex hormone, including estradiol. Estradiol is the major steroidal estrogen found in women's serum, which is mainly secreted by the ovary.

The estrogen receptor (ER) includes the receptor subtype ER-α (estrogen receptor alpha) and ER-β (estrogen receptor beta). There are also receptors (ERRs) closely related to the structure of the estrogen receptor, such as ERR-α, ERR-β and ERR-γ. The steroid nuclear receptor plays an important role in the physiological functions of the body, including transport homeostasis in relation to electrolyte and water balance, growth and development, wound healing, fertility, stress response, immune function and cognitive function. Thus, compounds containing modulators (i.e., antagonists, agonists, partial antagonists and partial agonists) that modulate the activity of the steroid nuclear receptor are capable of treating and preventing diseases that are affected by the steroid nuclear receptor activity. For example, the estrogen receptor ER-β exists in tissues such as the brain, bone, immune system, gastrointestinal tract, lung, ovary, endometrium, prostate, vascular system, genitourinary tract, salivary gland, etc. Therefore, the diseases associated with these tissues can be treated by modulators of selective ligand of ER-β receptor. ER-β acts as an antagonist to the ER-α receptor by heterodimerization with the estrogen receptor ER-α. For example, an ER-β receptor agonist can prevent the estrogen receptor ER-α from promoting the proliferation of tumors in prostate cancer and breast cancer tissues.

It is well known that endogenous estrogen has a great influence on the vascular system of premenopausal women and also has a protective effect on the myocardium. Estrogen directly affects the diastolic function of various vascular tissues (i.e., reduces vasoconstriction or vascular tension), reduces systemic vascular resistance, and improves microvascular circulation. Estrogen also reduces vascular cell proliferation and migration, reduces vascular reactivity and viscosity, and slows fibrosis of blood vessels. ER-β receptor agonist may have therapeutic effects on hypertension and various other cardiovascular diseases such as atherosclerosis and congestive heart failure.

ER-β receptor agonist also has antioxidant activity. In the process of oxidative phosphorylation in the body, various unstable molecules such as reactive oxide species, superoxide (O2-) and hydrogen peroxide ($H_2O_2$) are produced. These reactive oxygen species can oxidize endogenous macromolecules such as DNA, lipids and proteins thereby causing damage to their functions. The accumulation of this oxidative damage over time can lead to a variety of age-related diseases. For example, neurodegenerative diseases include Alzheimer's disease, Parkinson's disease, Huntington's disease, multiple sclerosis, amyotrophic lateral sclerosis, and various types of cancers, including prostate and colon diseases, vascular diseases such as stroke, and various age-related atherosclerosis. Ascorbic acid (vitamin C), tea polyphenols derived from red wine, and phytoestrogens such as genistein and coumestrol derived from soy products have the function of eliminating active oxygen in the body. ER-β receptor agonist is a polyphenolic compound which has antioxidant activity. Non-steroidal small molecules as ER-β receptor agonists have been reported in many literatures and patents. However, a polyhydroxyphthalazinone compound as a ER-β receptor agonist has not been reported yet.

SUMMARY

In order to overcome the disadvantages of the prior art, the object of the present disclosure is to provide a novel polyhydroxyphthalazinone compound.

To achieve the above object, the present disclosure provides the following technical solutions:

A polyhydroxyphthalazinone compound, wherein the chemical structure thereof is as presented in formula (I):

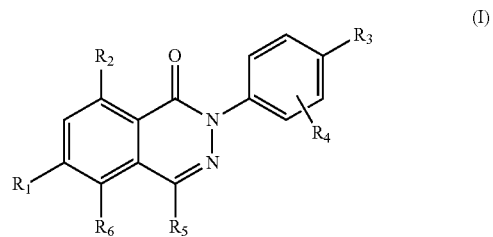

wherein R1, R2, R3 and R4 are each independently hydrogen, hydroxy, C1-3 alkoxy or halogen; R5 is hydrogen, C1-4 alkyl, C1-4 halogenated alkyl, phenyl or cyano; R6 is hydrogen or halogen. The halogen is fluorine, chlorine or bromine.

Preferably, R1, R2, and R3 are hydroxy, R4 and R6 are hydrogen; R5 is hydrogen, C1-4 alkyl, C1-4 halogenated alkyl, phenyl or cyano.

Preferably, R1, R2, and R3 are hydroxy, R4 and R6 are hydrogen; R5 is chlorine or bromine.

Preferably, R1, R2 and R3 are hydroxy; R4 is hydrogen or halogen; R5 is hydrogen; R6 is chlorine or bromine. The halogen is fluorine, chlorine or bromine.

A second object of the present disclosure is to provide a method of preparing the polyhydroxyphthalazinone compound. When R1, R2, and R3 are hydroxy, R4 and R6 are hydrogen, and R5 is hydrogen, C1-4 alkyl, C1-4 halogenated alkyl, phenyl or cyano, the method comprises the following steps:

reacting a compound (1) used as a starting material with an alkyl or phenyl Grignard reagent to produce a corresponding secondary alcohol compound (2);

brominating the secondary alcohol compound (2) to produce a compound (3);

performing a carboxylation reaction of the compound (3) to produce a compound (4);

oxidizing the compound (4) to produce a compound (5);

performing a condensation reaction of the compound (5) with the corresponding hydrazine to produce a compound (6);

demethylating the compound (6) to produce the target compound (7); and the synthetic scheme is as follows:

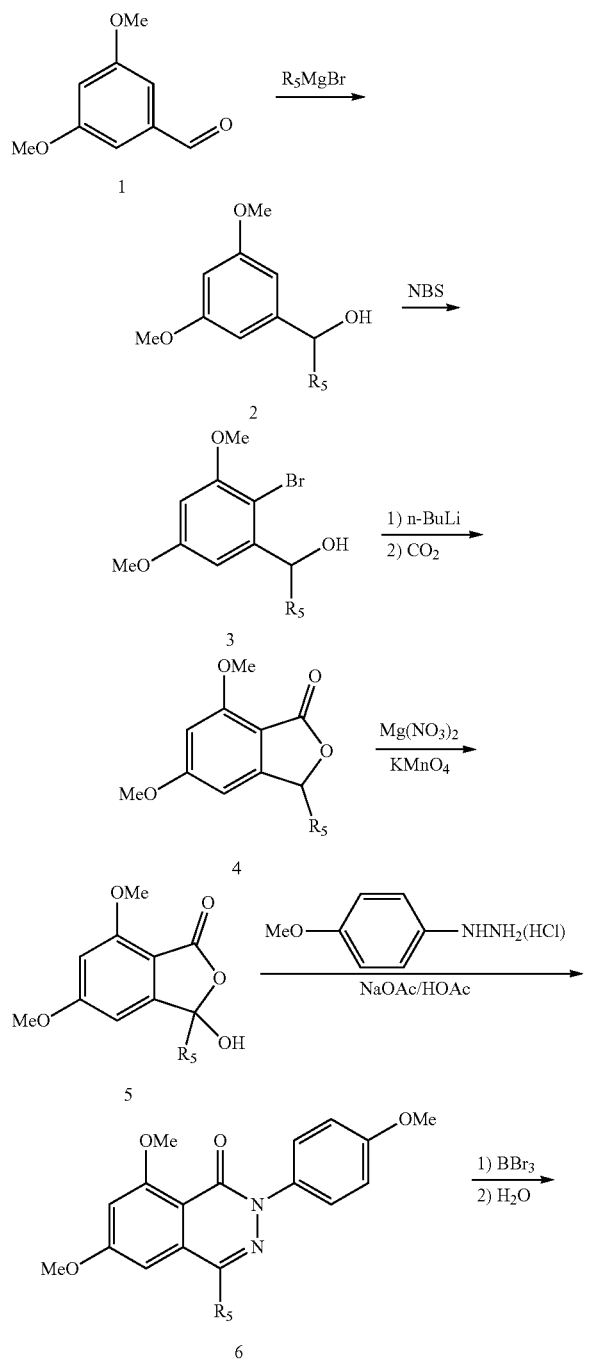

When R1, R2, and R3 are hydroxy, R4 and R6 are hydrogen, and R5 is chlorine or bromine, the method comprises the following steps:

performing a condensation of a compound (8) with a corresponding hydrazine to produce a compound (9);

halogenating the compound (9) to produce a intermediate (10);

demethylating the compound (10) to produce the target compound (11); and the synthetic scheme is as follows:

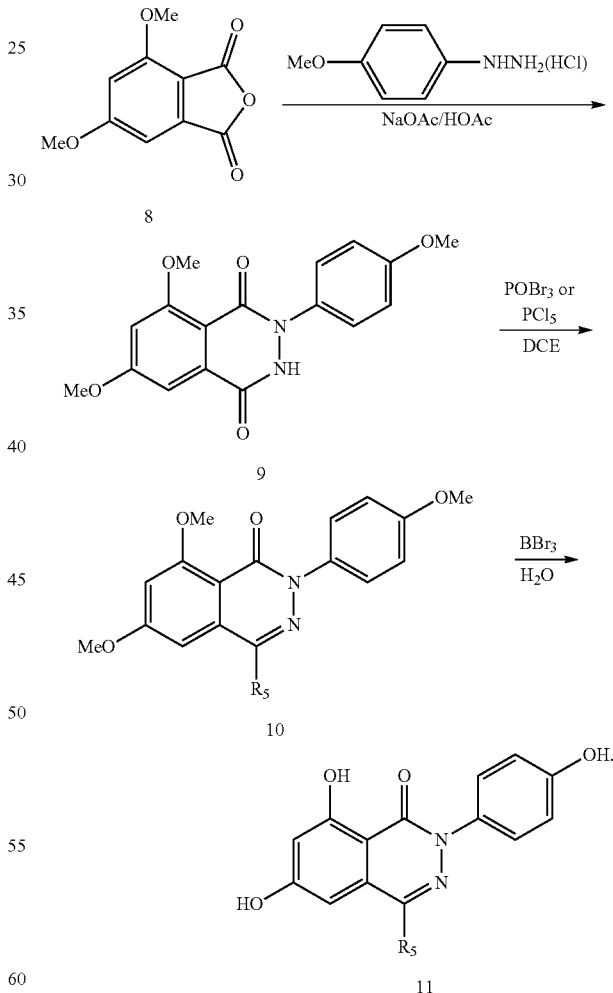

When R1, R2 and R3 are hydroxy, R4 is hydrogen or halogen, R5 is hydrogen, and R6 is chlorine or bromine, the method comprises the following steps:

reacting a compound (12) with bromosuccinimide or chlorosuccinimide to produce a compound (13);

demethylating the compound (13) to produce the target compound (14); and the synthetic scheme is as follows:

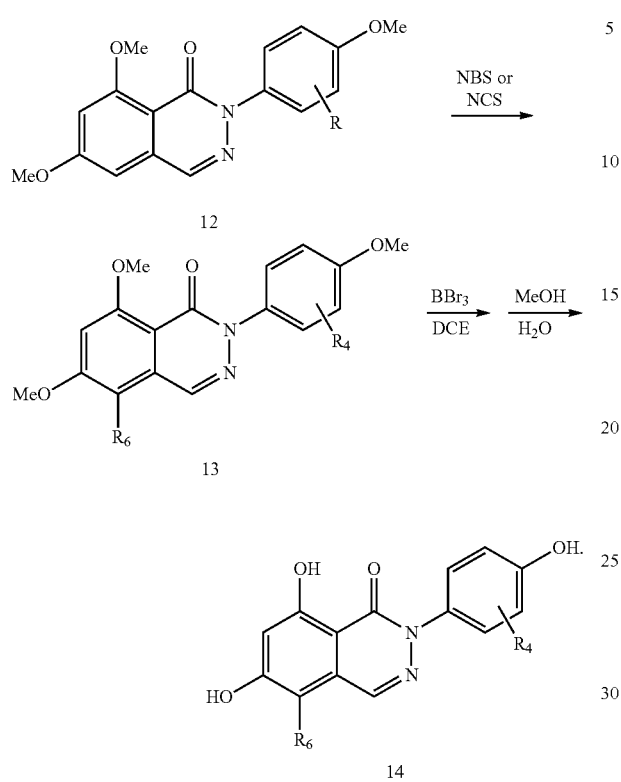

A third object of the present disclosure is to provide a use of the above polyhydroxyphthalazinone compound in the preparation of a drug for the treatment and/or prevention of estrogen-related diseases.

Preferably, the estrogen-related diseases include prostate disease, tumor, genitourinary tract disease, gastrointestinal disease, inflammation, osteoporosis, peripheral vascular disease, Alzheimer's disease, Parkinson's disease, stroke, eye disease, arthritis, menopausal hot flashes, cardiovascular disease, obesity and fatty liver.

A fourth object of the present disclosure is to provide a pharmaceutical composition comprising the above polyhydroxyphthalazinone compound or a salt thereof, and a pharmaceutically acceptable adjunct.

Compared with the prior art, the present disclosure discloses for the first time that a polyhydroxyphthalazinone compound has a good effect on activating ER-β receptor, and it is expected to develop a novel ER-β receptor agonist.

DETAILED DESCRIPTION

The technical solutions in the embodiments of the present disclosure are clearly described below. It is obvious that the described embodiments are only a part of the embodiments of the present disclosure, and not all of the embodiments. Based on the embodiments of the present disclosure, all other embodiments obtained by an ordinary person skilled in the art without creative efforts are within the scope of the present disclosure.

Example 1

6,8-dihydroxy-2-(4-hydroxyphenyl)-4-methyl-phthalazinone (C15H12N2O4)

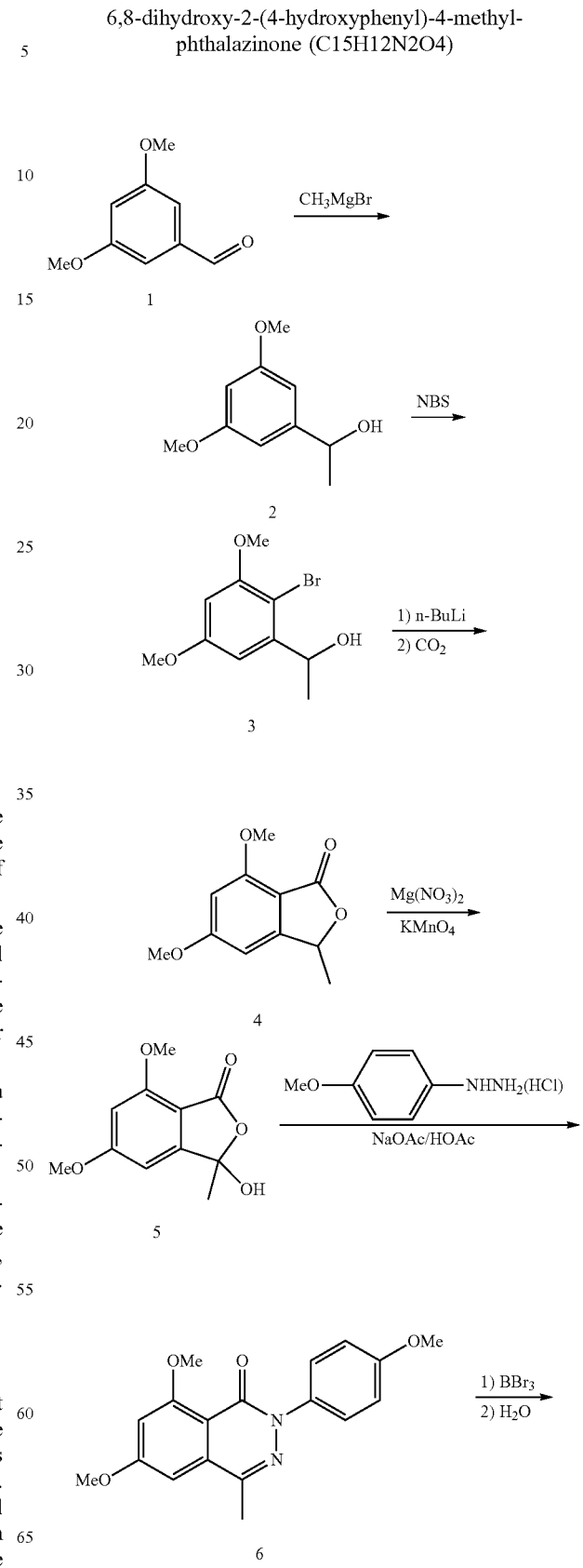

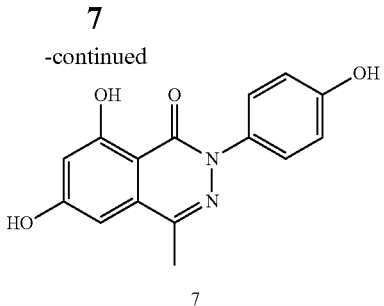

7

Step 1: 1.0 g of 3,5-dimethoxybenzaldehyde as the starting material was added into a 50 mL round-bottom flask, with 20 mL of anhydrous tetrahydrofuran as the solvent. 7.2 mmol of methylmagnesium bromide as Grignard reagent was added dropwise at −20° C., stirred, and the reaction time was 2.5-3.5 hours. The chromatography plate was used to determine the end of the reaction. After completion of the reaction, the mixture was hydrolyzed, extracted with ethyl acetate and concentrated to give an oily substance. The oily substance was separated and purified by silica gel column chromatography (dichloromethane:ethyl acetate=9:1) to give a white powdery substance, which was dried and weighed to give 1.0 g of 3,5-dimethoxyphenylethanol, with the yield of about 92%. Mass Spectrum: (ESI, positive) m/z [M+H]+ 183.09.

Step 2: 1.00 g of 3,5-dimethoxyphenylethanol and 1.17 g bromosuccinimide as the starting materials were added into a 50 mL round-bottom flask, with 30 mL of anhydrous chloroform as the solvent, stirred, and the reaction time was 6 hours. The chromatography plate was used to determine the end of the reaction. After completion of the reaction, the mixture was hydrolyzed, extracted with ethyl acetate and concentrated to give an oily substance. The oily substance was separated and purified by silica gel column chromatography (dichloromethane:ethyl acetate=9:1) to give a yellow powdery substance, which was dried and weighed to give 1.3 g of product, with the yield of about 91%. Mass Spectrum: (ESI, positive) m/z [M+H]+ 261.01.

Step 3: 17.4 g of 2-bromo-3,5-dimethoxyphenylethanol as the starting material was added into a 250 mL round-bottom flask, with 100 mL of anhydrous tetrahydrofuran as the solvent. 140 mmol of n-butyllithium was added dropwise at −78° C., stirred, and the reaction time was 2 hours. Then carbon dioxide was introduced. After completion of the reaction, the mixture was hydrolyzed, extracted with ethyl acetate and concentrated to give an oily substance. The oily substance was separated and purified by silica gel column chromatography (dichloromethane:ethyl acetate=9:2) to give a white powdery substance, which was dried and weighed to give 10.0 g of product, with the yield of about 72%. Mass Spectrum: (ESI, positive) m/z [M+H]+ 209.09.

Step 4: 500 mg of 5,7-dimethoxy-3-methyl-isophenylfuranone, 2 molar equivalents of manganese nitrate, 5 molar equivalents of potassium permanganate and 20 mL of water as the starting materials were added into a 50 mL round-bottom flask, stirred at 70-80° C., and the reaction time was 2 hours. The obtained mixture was extracted with ethyl acetate and concentrated to give an oily substance. The oily substance was separated and purified by silica gel column chromatography (dichloromethane:methanol=19:1) to give a white powdery substance, which was dried and weighed to give 250 mg of product, with the yield of about 46%. Mass Spectrum: (ESI, positive) m/z [M+H]+ 225.08.

Step 5: 2.0 g of 3-hydroxy-5,7-dimethoxy-3-methyl-isophenylfuranone, 1.1 molar equivalents of 4-methoxyphenylhydrazine hydrochloride and 1.2 molar equivalents of sodium acetate as the starting materials were added into a 50 mL round-bottom flask, with 20 mL of acetic acid as the solvent, stirred, and the reflux reaction time was 24 hours. The obtained mixture was concentrated, extracted with ethyl acetate and concentrated to give an oily substance. The oily substance was separated and purified by silica gel column chromatography (dichloromethane:methanol=19:1) to give a white powdery substance, which was dried and weighed to give 1.3 g of product, with the yield of about 45%. Mass Spectrum: (ESI, positive) m/z [M+H]+ 327.14.

Step 6: 500 mg of 6,8-dimethoxy-2-(4-methoxyphenyl)-4-methylphthalazinone and 5 molar equivalents of boron tribromide as the starting material were added into a 50 mL round-bottom flask, with 30 mL of 1,2-dichloroethane as the solvent, stirred, and the reflux reaction time was 24 hours. The obtained mixture was hydrolyzed by addition of methanol and water, extracted with dichloroethane, and concentrated to give an oily substance. The oily substance was separated and purified by silica gel column chromatography (dichloromethane:methanol=9:1) to give a white powdery substance, which was dried and weighed to give 300 mg of target product 6,8-dihydroxy-2-(4-hydroxyphenyl)-4-methylphthalazinone, with the yield of about 70%.

Nuclear magnetic resonance spectrum: $^1$H NMR (400 MHz, DMSO-d6) δ 12.70 (s, 1H, OH), 10.88 (s, 1H, OH), 9.74 (s, 1H, OH), 7.33 (d, J=8.8 Hz, 2H, ArH), 6.87 (d, J=8.8 Hz, 2H, ArH), 6.68 (s, 1H, ArH), 6.61 (s, 1H, ArH), 3.35 (s, 3H, CH$_3$); Mass Spectrum: (ESI, negative) m/e [M−H]− 283.23.

Example 2

4-ethyl-6,8-dihydroxy-2-(4-hydroxyphenyl)-phthalazinone ($C_{16}H_{14}N_2O_4$)

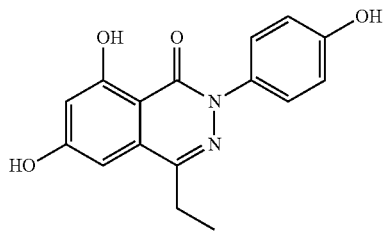 [SMILES: CCc1nn(-c2ccc(O)cc2)c(=O)c2c(O)cc(O)cc12]

The compound was obtained according to the synthesis method of Example 1 to give the white powdery substance.

Nuclear magnetic resonance spectrum: $^1$H NMR (400 MHz, DMSO-d6) δ 12.75 (s, 1H, OH), 10.87 (s, 1H, OH), 9.74 (s, 1H, OH), 7.36 (d, J=8.8 Hz, 2H, ArH), 6.86 (d, J=8.8 Hz, 2H, ArH), 6.73 (d, J=2.0 Hz, 1H, ArH), 6.60 (d, J=2.0 Hz, 1H, ArH), 2.86 (q, J=7.2 Hz, 2H, CH$_2$); 1.24 (t, J=7.2 Hz, 3H, CH$_3$); Mass Spectrum: (ESI, negative) m/e [M−H]− 297.18.

Example 3

6,8-dihydroxy-2-(4-hydroxyphenyl)-phthalazinone (C$_{14}$H$_{10}$N$_2$O$_4$)

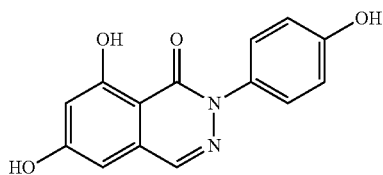 [SMILES: O=c1c2c(O)cc(O)cc2cnn1-c1ccc(O)cc1]

The compound was obtained with 3,5-dimethoxybenzyl alcohol as a starting material according to the synthesis method of Example 1 to give the white powdery substance.

Nuclear magnetic resonance spectrum: $^1$H NMR (400 MHz, DMSO-d6) δ 12.73 (s, 1H, OH), 10.88 (s, 1H, OH), 9.76 (s, 1H, OH), 8.07 (s, 1H, CH=N), 7.35 (d, J=8.8 Hz, 2H, ArH), 6.87 (d, J=8.8 Hz, 2H, ArH), 6.71 (d, J=2.0 Hz, 1H, ArH), 6.63 (d, J=2.0 Hz, 1H, ArH); Mass Spectrum: (ESI, negative) m/e [M−H]$^-$ 269.04.

Example 4

2-(3-fluoro-4-hydroxyphenyl)-6,8-dihydroxy-4methylphthalazinone (C$_{15}$H$_{11}$FN$_2$O$_4$)

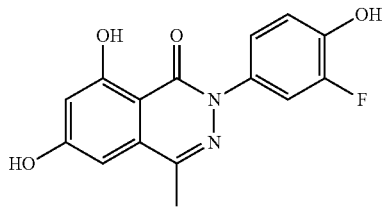 [SMILES: Cc1nn(-c2ccc(O)c(F)c2)c(=O)c2c(O)cc(O)cc12]

The compound was obtained according to the synthesis method of Example 1 to give the corresponding white powdery substance.

Nuclear magnetic resonance spectrum: $^1$H NMR (400 MHz, DMSO-d6) δ 12.73 (s, 1H, OH), 10.87 (s, 1H, OH), 10.25 (s, 1H, OH), 7.45 (dd, 1H, J=11.7, 2.4 Hz, ArH), 7.17-7.03 (m, 2H, ArH), 6.67 (s, 1H, ArH), 6.62 (s, 1H, ArH), 3.36 (s, 3H, CH$_3$); Mass Spectrum: (ESI, negative) m/e [M−H]$^-$ 301.06.

Example 5

6,8-dihydroxy-2-(4-hydroxyphenyl)-4-phenyl-phthalazinone (C$_{20}$H$_{14}$N$_2$O$_4$)

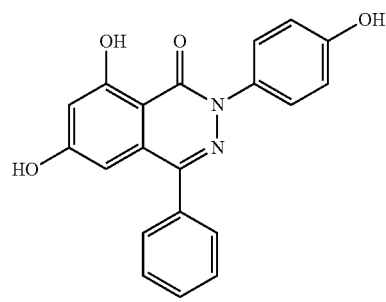 [SMILES: O=c1c2c(O)cc(O)cc2c(-c2ccccc2)nn1-c1ccc(O)cc1]

The compound was obtained with 3,5-dimethoxybenzaldehyde and phenyl Grignard reagent as starting materials according to the synthesis method of Example 1 to give the white powdery substance.

Nuclear magnetic resonance spectrum: $^1$H NMR (400 MHz, DMSO-d6) δ 12.70 (s, 1H, OH), 10.86 (s, 1H, OH), 9.73 (s, 1H, OH), 7.53-7.38 (m, 5H, ArH), 7.33 (d, J=8.8 Hz, 2H, ArH), 6.86 (d, J=8.8 Hz, 2H, ArH), 6.72 (d, J=2.0 Hz, 1H, ArH), 6.62 (d, J=2.0 Hz, 1H, ArH); Mass Spectrum: (ESI, negative) m/e [M−H]$^-$ 345.11.

Example 6

4-bromo-6,8-dihydroxy-2(4-hydroxyphenyl)phthalazinone (C$_{14}$H$_9$BrN$_2$O$_4$)

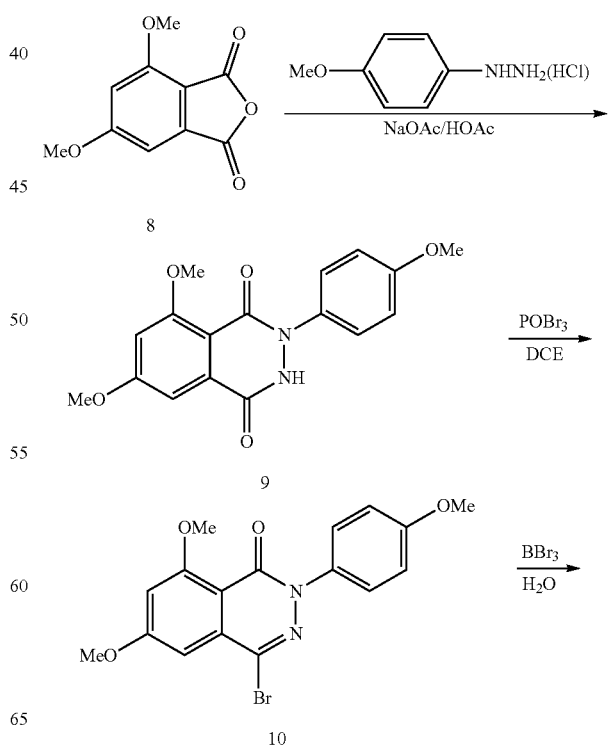

-continued

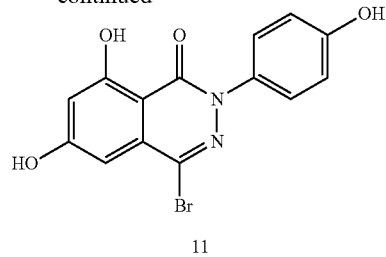

11

Step 1: 1.0 g of 4,6-dimethoxy-isobenzofuran-1,3-dione, 1.1 molar equivalents of 4-methoxyphenylhydrazine hydrochloride and 1.2 molar equivalents of sodium acetate as the starting materials were added into a 50 mL round-bottom flask, with 20 mL of acetic acid as the solvent, stirred, and the reflux reaction time was 24 hours. The mixture was concentrated, extracted with ethyl acetate and concentrated to give an oily substance. The oily substance was separated and purified by silica gel column chromatography (dichloromethane methanol=19:1) to give a white powdery substance, which was dried and weighed to give 0.89 g of product, with the yield of about 56%. Mass Spectrum: (ESI, positive) m/z [M+H]$^+$329.14.

Step 2: 500 mg of 6,8-dimethoxy-2-(4-methoxy-phenyl)-2,3-dihydro-phthalazine-1,4-dione and 2 molar equivalents of phosphorus oxybromide as the starting materials were added into a 50 mL round-bottom flask, with 30 mL of 1,2-dichloroethane as the solvent, stirred, and the reflux reaction time was 24 hours. The obtained mixture was hydrolyzed by addition of water, neutralized with sodium hydrogencarbonate, extracted with dichloromethane, and concentrated to give an oily substance. The oily substance was separated and purified by silica gel column chromatography (ethyl acetate:hexane=4:1) to give a white powdery substance, which was dried and weighed to give 270 mg of target product 4-bromo-6,8-dimethoxy-2-(4-methoxy-phenyl)-2,3-dihydro-phthalazine-1,4-dione, with the yield of about 45%. Mass Spectrum: (ESI, positive) m/z [M+H]$^+$ 391.04.

Step 3: 500 mg of 4-bromo-6,8-dimethoxy-2-(4-methoxyphenyl)-2,3-dihydro-phthalazine-1,4-dione and 5 molar equivalents of boron tribromide as the starting materials were added into a 50 mL round-bottom flask, with 30 mL of 1,2-dichloroethane as the solvent, stirred, and the reflux reaction time was 24 hours. The obtained mixture was hydrolyzed by addition of methanol and water, extracted with dichloromethane, and concentrated to give an oily substance. The oily substance was separated and purified by silica gel column chromatography (dichloromethane:methanol=9:1) to give a white powdery substance, which was dried and weighed to give 340 mg of target product 4-bromo-6,8-dihydroxy-2-(4-hydroxyphenyl) phthalazinone, with the yield of about 76%.

Nuclear magnetic resonance spectrum: $^1$H NMR (400 MHz, DMSO-d6) δ 12.78 (s, 1H, OH), 10.87 (s, 1H, OH), 9.74 (s, 1H, OH), 7.32 (d, J=8.8 Hz, 2H, ArH), 6.86 (d, J=8.8 Hz, 2H, ArH), 6.70 (d, J=2.0 Hz, 1H, ArH), 6.61 (d, J=2.0 Hz, 1H, ArH); Mass Spectrum: (ESI, negative) m/e [M−H]$^−$ 348.13.

Example 7

4-chloro-6,8-dihydroxy-2-(4-hydroxyphenyl) phthalazinone (C$_{14}$H$_9$ClN$_2$O$_4$)

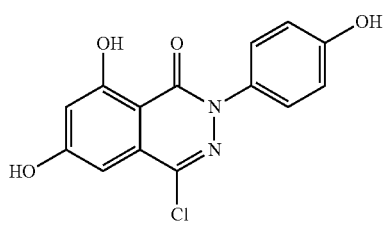 [SMILES: O=c1c2c(O)cc(O)cc2c(Cl)nn1-c1ccc(O)cc1]

The compound was obtained according to the synthesis method of Example 6 to give the white powdery substance.

Nuclear magnetic resonance spectrum: $^1$H NMR (400 MHz, DMSO-d6) δ 12.75 (s, 1H, OH), 10.86 (s, 1H, OH), 9.77 (s, 1H, OH), 7.33 (d, J=8.8 Hz, 2H, ArH), 6.88 (d, J=8.8 Hz, 2H, ArH), 6.72 (d, J=2.0 Hz, 1H, ArH), 6.61 (d, J=2.0 Hz, 1H, ArH); Mass Spectrum: (ESI, negative) m/e [M−H]$^−$ 303.04.

Example 8

4-bromo-2-(3-fluoro-4-hydroxyphenyl)-6,8-dihydroxyphthalazinone (C$_{14}$H$_8$BrFN$_2$O$_4$)

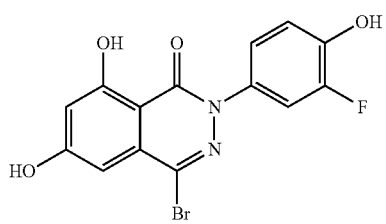 [SMILES: O=c1c2c(O)cc(O)cc2c(Br)nn1-c1ccc(O)c(F)c1]

The compound was obtained according to the synthesis method of Example 6 to give the white powdery substance.

Nuclear magnetic resonance spectrum: $^1$H NMR (400 MHz, DMSO-d6) δ 12.78 (s, 1H, OH), 10.88 (s, 1H, OH), 10.28 (s, 1H, OH), 7.42 (dd, J=11.7, 2.4 Hz, 1H, ArH), 7.17-7.04 (m, 2H, ArH), 6.71 (d, J=2.0 Hz, 1H, ArH); 6.62 (d, J=2.0 Hz, 1H, ArH); Mass Spectrum: (ESI, negative) m/e [M−H]$^−$ 364.98.

Example 9

5-bromo-2-(4-hydroxyphenyl)-6,8-dihydroxyphthalazinone (C$_{14}$H$_9$BrN$_2$O$_4$)

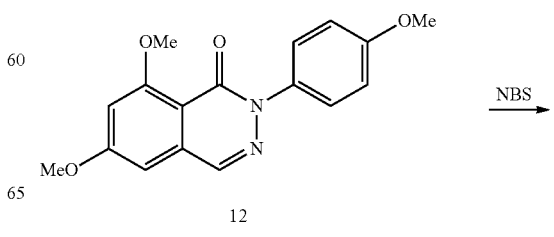

12

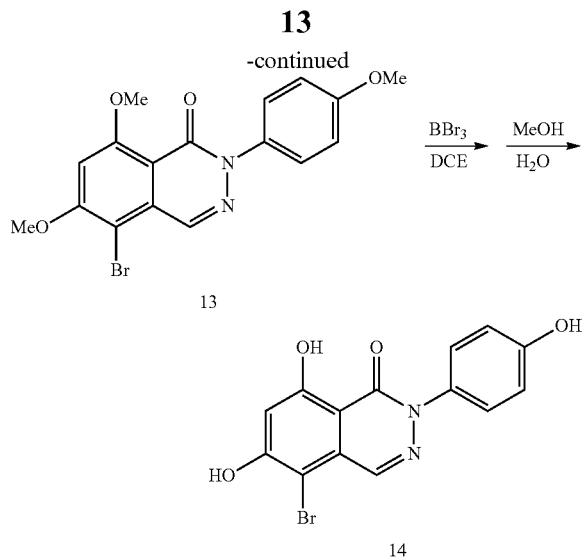

Step 1: 500 mg of 6,8-dimethoxy-2-(4-methoxyphenyl)phthalazinone and 1.2 equivalents of bromosuccinimide as the starting materials were added into a 50 mL round-bottom flask, with 30 mL of anhydrous tetrahydrofuran as the solvent, stirred, and the reflux reaction time was 24 hours. The obtained mixture was concentrated, extracted with ethyl acetate and concentrated to give an oily substance. The oily substance was separated and purified by silica gel column chromatography (dichloromethane:methanol=19:1) to give a white powdery substance, which was dried and weighed to give 0.51 g of product, with the yield of about 81%. Mass Spectrum: (ESI, positive) m/z [M+H]$^+$ 391.04.

Step 2: 500 mg of 5-bromo-6,8-dimethoxy-2-(4-methoxyphenyl)phthalazinone and 5 equivalents of boron tribromide as the starting materials were added into a 50 mL round-bottom flask, with 30 mL of 1,2-dichloroethane as the solvent, stirred, and the reflux reaction time was 24 hours. The obtained mixture was hydrolyzed by addition of methanol and water, extracted with dichloroethane, and concentrated to give an oily substance. The oily substance was separated and purified by silica gel column chromatography (dichloromethane methanol=9:1) to give a white powdery substance, which was dried and weighed to give 355 mg of target product 5-bromo-6,8-dihydroxy-2-(4-hydroxyphenyl)phthalazine, with the yield of about 79%.

Nuclear magnetic resonance spectrum: $^1$H NMR (400 MHz, DMSO-d6) δ 12.88 (s, 1H, OH), 11.38 (s, 1H, OH), 9.78 (s, 1H, OH), 8.06 (s, 1H, CH=N), 7.36 (d, J=8.8 Hz, 2H, ArH), 6.86 (d, J=8.8 Hz, 2H, ArH), 6.53 (s, 1H, ArH); Mass Spectrum: (ESI, negative) m/e [M−H]$^-$ 346.96.

Example 10

The activity of the compound was obtained as follows: the compound was first dissolved in DMSO and formulated into 6-8 concentration gradient solutions. The estrogen receptor and radiolabeled estradiol ([$^3$H]-estradiol, 100 nM) were added into the buffer and mixed to prepare a reaction solution. Each compound concentration gradient solution was separately added into the reaction solution, mixed, and incubated overnight at 4° C. so that the compound and estradiol fully reacted with the estrogen receptor. Then, the TopCount NXT Liquid Scintillation Counter (Perkin Elmer) was used for the radioactivity intensity measurement after GF/B filtration. Data processing was performed according to the detected values of each concentration to obtain the affinity constant of the compound with estrogen receptor, as shown in the following table:

TABLE 1

| Compound | Affinity constant of ER-β receptor (nM) | Affinity constant of ER-α receptor (nM) |
|---|---|---|
| (structure 1) | 105 | 1200 |
| (structure 2) | 8 | 76 |
| (structure 3) | 10 | 98 |
| (structure 4) | 1500 | 3600 |

The above is only the preferred embodiments of the present disclosure and is not intended to limit the present disclosure. Any modifications, equivalent substitutions, improvements, etc. made within the spirit and the scope of the present disclosure are intended to be included within the scope of the present disclosure.

The invention claimed is:

1. A polyhydroxyphthalazinone compound of formula (I):

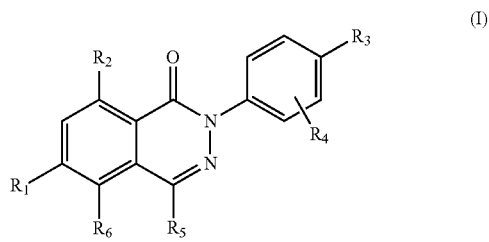

wherein $R_1$, $R_2$ and $R_3$ are hydroxy; $R_4$ and $R_6$ are hydrogen or halogen, $R_5$ is hydrogen, $C_{1-4}$ alkyl, $C_{1-4}$ halogenated alkyl, phenyl, halogen or cyano.

2. The polyhydroxyphthalazinone compound according to claim 1, wherein $R_1$, $R_2$ and $R_3$ are hydroxy, $R_4$ and $R_6$ are hydrogen; $R_5$ is hydrogen, $C_{1-4}$ alkyl, $C_{1-4}$ halogenated alkyl, phenyl or cyano.

3. The polyhydroxyphthalazinone compound according to claim 1, wherein $R_1$, $R_2$ and $R_3$ are hydroxy, $R_4$ and $R_6$ are hydrogen; $R_5$ is chlorine or bromine.

4. The polyhydroxyphthalazinone compound according to claim 1, wherein $R_1$, $R_2$ and $R_3$ are hydroxy; $R_4$ is hydrogen or halogen; $R_5$ is hydrogen; $R_6$ is chlorine or bromine.

5. A method of preparing the polyhydroxyphthalazinone compound according to claim 2, comprising the following steps:
   reacting a compound (1) used as a starting material with an alkyl or phenyl Grignard reagent to produce a corresponding secondary alcohol compound (2);
   brominating the secondary alcohol compound (2) to produce a compound (3);
   performing a carboxylation reaction of the compound (3) to produce a compound (4);
   oxidizing the compound (4) to produce a compound (5);
   performing a condensation reaction of the compound (5) with a corresponding hydrazine to produce a compound (6);
   demethylating the compound (6) to produce the target compound (7); and the synthetic scheme is as follows:

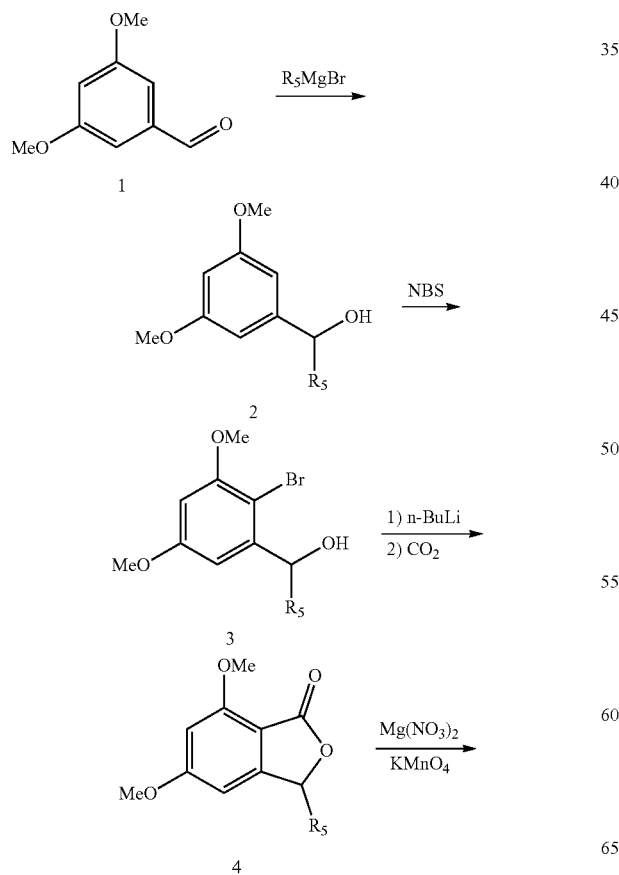

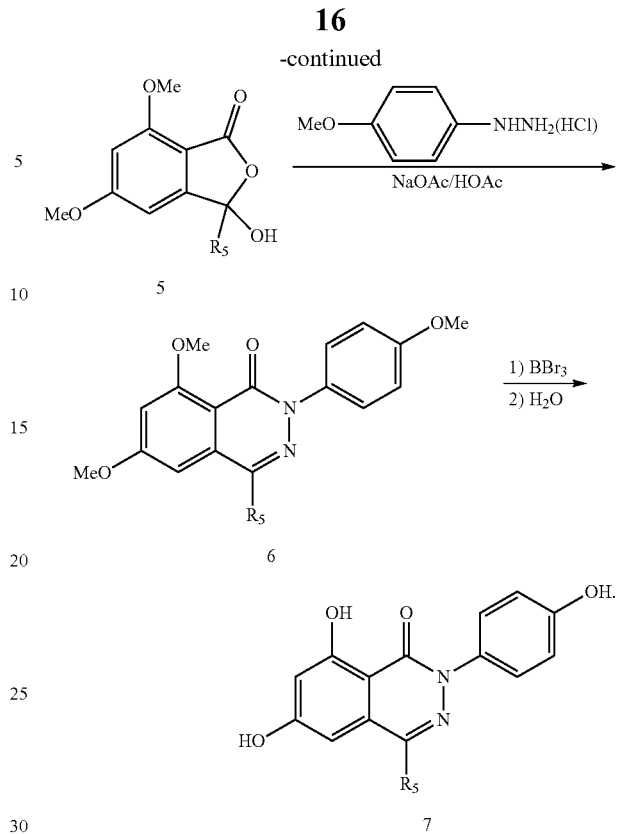

6. A method of preparing the polyhydroxyphthalazinone compound according to claim 3, comprising the following steps:
   performing a condensation of a compound (8) with a corresponding hydrazine to produce a compound (9);
   halogenating the compound (9) to produce a intermediate (10);
   demethylating the compound (10) to produce the target compound (11); and the synthetic scheme is as follows:

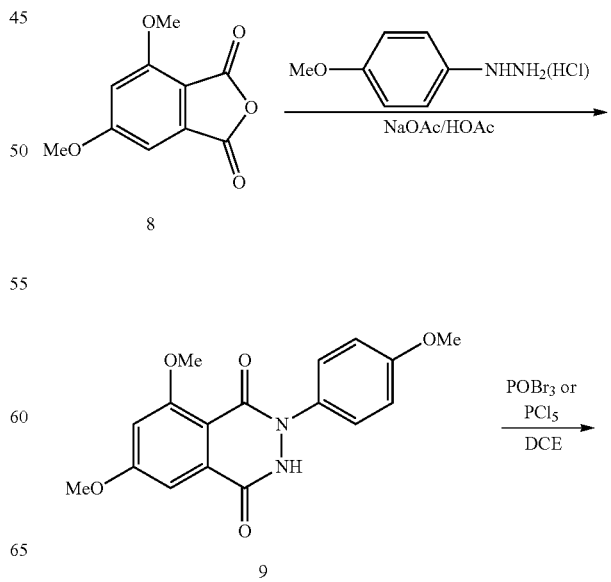

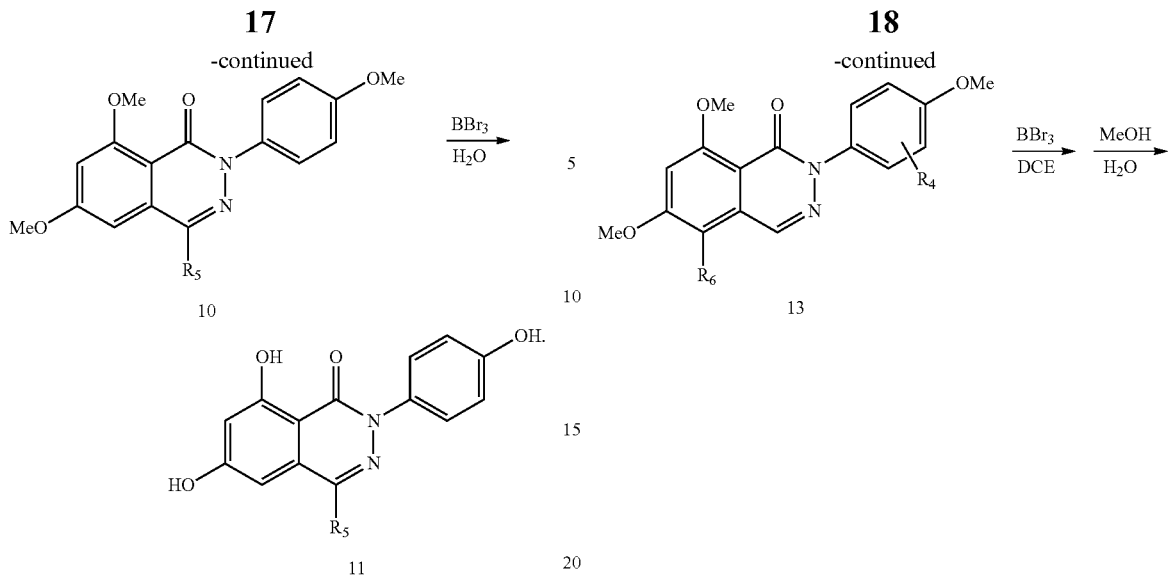

7. A method of preparing the polyhydroxyphthalazinone compound according to claim 4, comprising the following steps:
   reacting a compound (12) with bromosuccinimide or chlorosuccinimide to produce a compound (13);
   demethylating the compound (13) to produce the target compound (14); and the synthetic scheme is as follows:

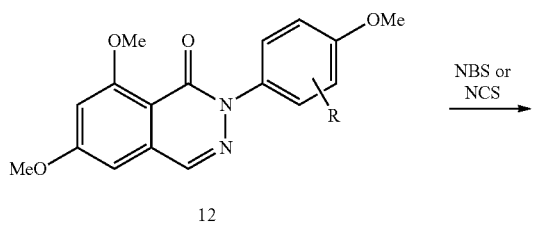

8. A pharmaceutical composition, comprising the polyhydroxyphthalazinone compound according to claim 1 or a salt thereof, and a pharmaceutically acceptable adjunct.

* * * * *